United States Patent
Saygili

(10) Patent No.: US 10,772,357 B2
(45) Date of Patent: Sep. 15, 2020

(54) CARTRIDGE ASSEMBLY FOR AN AEROSOL-GENERATING SYSTEM AND AN AEROSOL-GENERATING SYSTEM COMPRISING A CARTRIDGE ASSEMBLY

(71) Applicant: Philip Morris Products S.A., Neuchatel (CH)

(72) Inventor: Ali Murat Saygili, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 404 days.

(21) Appl. No.: 15/750,929

(22) PCT Filed: Aug. 18, 2016

(86) PCT No.: PCT/EP2016/069662
§ 371 (c)(1),
(2) Date: Feb. 7, 2018

(87) PCT Pub. No.: WO2017/032695
PCT Pub. Date: Mar. 2, 2017

(65) Prior Publication Data
US 2018/0228216 A1 Aug. 16, 2018

(30) Foreign Application Priority Data
Aug. 21, 2015 (EP) ................................. 15182012

(51) Int. Cl.
*A24F 40/40* (2020.01)
*A24F 40/10* (2020.01)
(Continued)

(52) U.S. Cl.
CPC .......... *A24F 47/008* (2013.01); *A24B 15/167* (2016.11); *A24F 7/00* (2013.01);
(Continued)

(58) Field of Classification Search
None
See application file for complete search history.

(56) References Cited

U.S. PATENT DOCUMENTS

| 2006/0283468 A1 | 12/2006 | Lipowicz |
| 2008/0241255 A1 | 10/2008 | Rose et al. |

(Continued)

FOREIGN PATENT DOCUMENTS

| CN | 1297383 A | 5/2001 |
| CN | 204191590 U | 3/2015 |

(Continued)

OTHER PUBLICATIONS

Combined Chinese Office Action and Search Report dated Mar. 23, 2020 in Chinese Patent Application No. 201680046102.4, citing documents AO, AP and AQ therein, 12 pages.

(Continued)

*Primary Examiner* — Michael J Felton
(74) *Attorney, Agent, or Firm* — Oblon, McClelland, Maier & Neustadt, L.L.P.

(57) ABSTRACT

A cartridge assembly for an aerosol-generating system, including a cartridge including a first compartment having a first air inlet and outlet, a second compartment having a second air inlet and outlet, and a mouthpiece partially surrounding the cartridge and having a third air outlet, the cartridge and the mouthpiece being longitudinally movable relative to one another between a retracted position and an extended position creating a chamber therebetween in fluid communication with the first, second, and third air outlets, the air inlets and the first and second air outlets are obstructed by the mouthpiece in the retracted position, the third air outlet is obstructed by the cartridge, and in the extended position air is drawable into the chamber along first and second airflow pathways extending from the respec- (Continued)

tive air inlet through the compartment to the air outlet, and out of the chamber through the third air outlet.

15 Claims, 3 Drawing Sheets

(51) Int. Cl.
    *A24F 47/00*     (2020.01)
    *A61M 15/06*     (2006.01)
    *A61M 15/00*     (2006.01)
    *A61M 11/04*     (2006.01)
    *A24B 15/167*     (2020.01)
    *A24F 7/00*     (2006.01)

(52) U.S. Cl.
    CPC .............. *A24F 40/10* (2020.01); *A24F 40/40* (2020.01); *A61M 11/042* (2014.02); *A61M 15/0003* (2014.02); *A61M 15/06* (2013.01); *A61M 2205/3653* (2013.01)

(56) References Cited

U.S. PATENT DOCUMENTS

| | | |
|---|---|---|
| 2013/0074854 A1 | 3/2013 | Lipowicz |
| 2014/0345630 A1 | 11/2014 | Lipowicz |
| 2016/0227839 A1 | 8/2016 | Zuber et al. |
| 2016/0250201 A1 | 9/2016 | Rose et al. |

FOREIGN PATENT DOCUMENTS

| | | |
|---|---|---|
| RU | 2 393 883 C1 | 7/2010 |
| WO | 2006/070288 A2 | 7/2006 |
| WO | WO 2007/123046 A1 | 11/2007 |
| WO | 2008/121610 A1 | 10/2008 |
| WO | 2013/083635 A1 | 6/2013 |
| WO | WO 2015/000974 A1 | 1/2015 |
| WO | 2015/040180 A2 | 3/2015 |
| WO | WO 2015/197627 A1 | 12/2015 |

OTHER PUBLICATIONS

Combined Russian Office Action and Search Report dated Sep. 16, 2019 in corresponding Chinese Patent Application No. 2018109725 (with English Translation and English Translation of Category of Cited Documents) citing document AO therein, 9 pages.
International Search Report and Written Opinion dated Oct. 10, 2016 in PCT/EP2016/069662 filed Aug. 18, 2016.

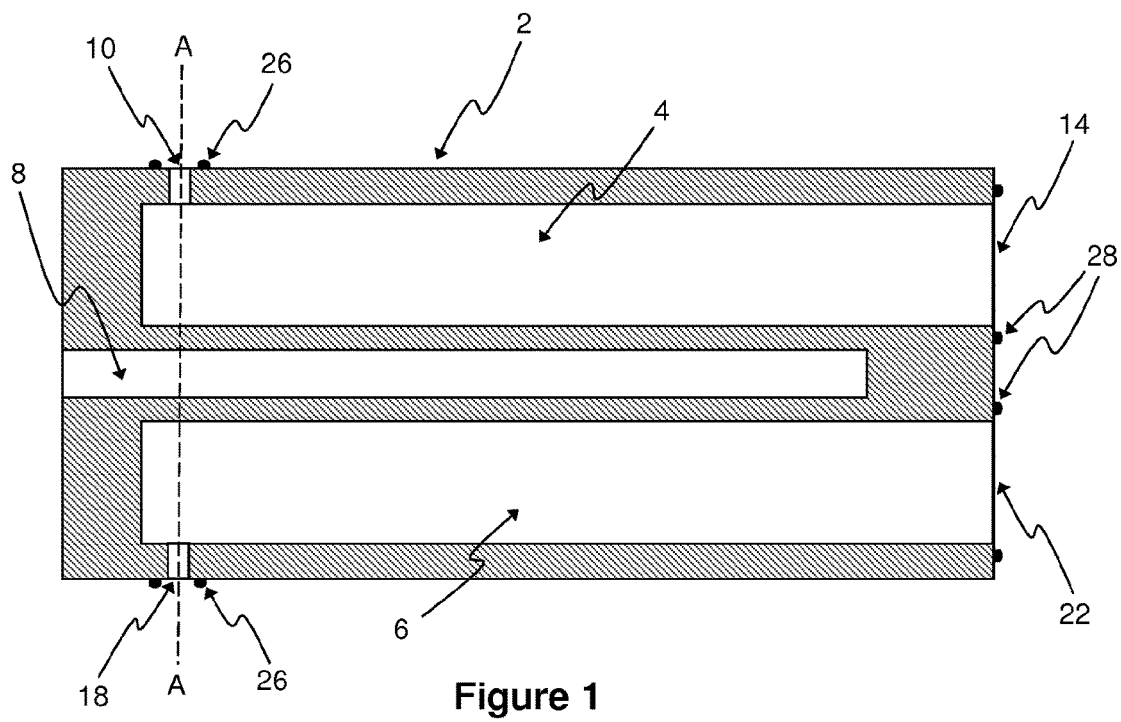
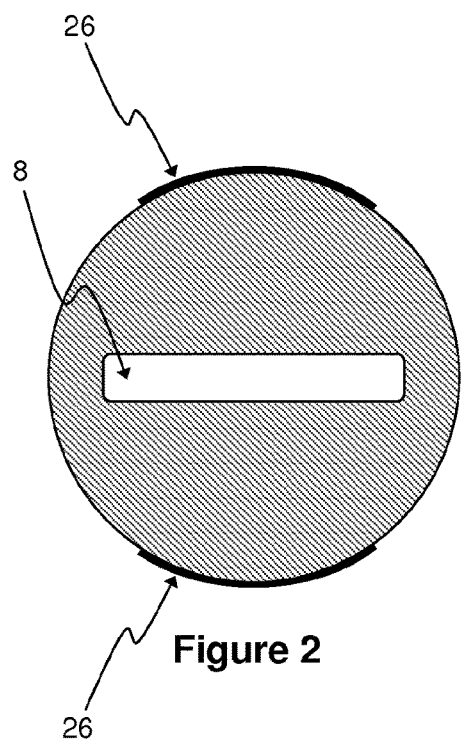
Figure 2
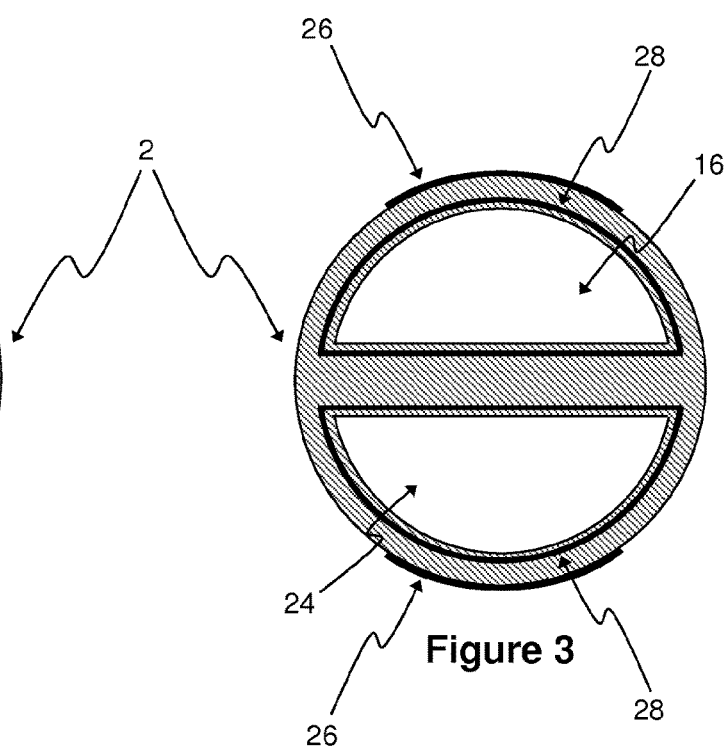
Figure 3
Figure 1

CARTRIDGE ASSEMBLY FOR AN AEROSOL-GENERATING SYSTEM AND AN AEROSOL-GENERATING SYSTEM COMPRISING A CARTRIDGE ASSEMBLY

The invention relates to a cartridge assembly for use in an aerosol-generating system and an aerosol-generating system comprising such a cartridge assembly. Particularly preferred embodiments of the invention relate to a cartridge assembly comprising a nicotine source and acid source for use in an aerosol-generating system for the in situ generation of an aerosol comprising nicotine salt particles and an aerosol-generating system comprising such a cartridge assembly.

Devices for delivering nicotine to a user comprising a nicotine source and a volatile delivery enhancing compound source are known. For example, WO 2008/121610 A1 discloses devices in which nicotine and a volatile acid, such as pyruvic acid, are reacted with one another in the gas phase to form an aerosol of nicotine salt particles that is inhaled by the user.

Nicotine sources and volatile delivery enhancing compound sources for use in aerosol-generating systems of the type disclosed in WO 2008/121610 A1 will have a tendency to lose nicotine and volatile delivery enhancing compound, respectively, when stored for any length of time. To ensure sufficient nicotine and volatile delivery enhancing compound are retained during storage to generate a desired aerosol of nicotine salt particles for delivery to a user, it has been proposed to manufacture aerosol-generating systems of the type disclosed in WO 2008/121610 A1 in which the nicotine source and volatile delivery enhancing compound source are housed in compartments that are sealed by one or more removable or frangible barriers prior to initial use of the aerosol-generating system.

For example, WO 2015/000974 A1 discloses an aerosol-generating system comprising a housing having a first portion and a second portion, which are movable relative to one another between an open position and a closed position, in which the housing comprises a first compartment comprising a nicotine source and a second compartment comprising a volatile delivery enhancing compound source, which are initially sealed by one or more removable or frangible barriers.

However, the inclusion of one or more removable or frangible barriers may disadvantageously increase the cost and complexity of manufacturing such aerosol-generating systems. Consequently, it would be desirable to provide an aerosol-generating system for the in situ generation of an aerosol comprising nicotine salt particles in which sufficient nicotine and volatile delivery enhancing compound may be retained during storage without the use of removable or frangible barriers.

According to the invention there is provided a cartridge assembly having a proximal end and a distal end for use in an aerosol-generating system, the cartridge assembly comprising: a cartridge comprising: a first compartment having a first air inlet and a first air outlet; and a second compartment having a second air inlet and a second air outlet, and a mouthpiece partially surrounding the cartridge, the mouthpiece having a third air outlet. The cartridge and the mouthpiece are longitudinally movable relative to one another between a retracted position in which a proximal end of the mouthpiece abuts a proximal end of the cartridge, and an extended position in which the proximal ends of the mouthpiece and the cartridge are longitudinally spaced apart so as to create a chamber therebetween in fluid communication with the first, second and third air outlets. In the retracted position the first and second air inlets and the first and second air outlets are obstructed by the mouthpiece and the third air outlet is obstructed by the cartridge. In the extended position air may be drawn into the chamber along a first airflow pathway extending from the first air inlet, through the first compartment, to the first air outlet and a second airflow pathway extending from the second air inlet, through the second compartment, to the second air outlet, and out of the chamber through the third air outlet.

According to the invention there is also provided an aerosol-generating system comprising the cartridge assembly and an aerosol-generating device comprising a heater for heating one or both of the first and second compartments of the cartridge of the cartridge assembly.

As used herein with reference to the invention, the term "air inlet" is used to describe one or more apertures through which air may be drawn into a component or portion of a component of the cartridge assembly.

As used herein with reference to the invention, the term "air outlet" is used to describe one or more apertures through which air may be drawn out of a component or portion of a component of the cartridge assembly.

As used herein with reference to the invention, by "obstructed" it is meant that an air inlet or an air outlet is blocked such that airflow into or out of a component or portion of a component of the cartridge assembly through the air inlet or the air outlet is substantially prevented.

The cartridge and the mouthpiece of the cartridge assembly of the invention are longitudinally movable relative to one another from the retracted position to the extended position. The cartridge and the mouthpiece of the cartridge assembly are also movable relative to one another from the extended position to the retracted position. The retracted position may also be referred to as the closed position or 'off' position and the extended position may also be referred to as the open position or 'on' position.

There are two air flow pathways through the cartridge of the cartridge assembly of the invention, a first airflow pathway extending from the first air inlet, through the first compartment, to the first air outlet, and a second airflow pathway extending from the second air inlet, through the second compartment, to the second air outlet.

In the extended position the first and second airflow pathways through the cartridge are both unobstructed and the first and second air outlets of the first and second compartments, respectively of the cartridge are in fluid communication with a chamber between the proximal end of the cartridge and the proximal end of the mouthpiece.

As used herein with reference to the invention, by "unobstructed" it is meant that a first air stream may be drawn into the cartridge through the first air inlet, along the first airflow pathway through the first compartment between the first air inlet and the first air outlet, and out of the cartridge through the first air outlet, and a second air stream may be drawn into the cartridge through the second air inlet, along the second airflow pathway through the second compartment between the second air inlet and the second air outlet, and out of the cartridge through the second air outlet.

In the extended position, the third air outlet of the mouthpiece is also unobstructed and in fluid communication with the chamber between the proximal end of the cartridge and the proximal end of the mouthpiece.

Advantageously, in use, in the extended position this allows one or more first reagents housed in the first compartment to be entrained in a first air stream drawn along the first airflow pathway into the chamber and one or more second reagents housed in the second compartment to be entrained in a second air stream drawn along the second airflow pathway into the chamber. The first reagents entrained in the first air stream and the second reagents entrained in the air second air stream may react with one another in the gas phase in the chamber to form an aerosol that may be drawn out of the cartridge assembly through the third air outlet of the mouthpiece for delivery to a user.

Longitudinal movement of the cartridge and the mouthpiece of the cartridge assembly of the invention relative to one another from the retracted position to the extended position thus advantageously provides a reaction chamber in which an aerosol may be generated in situ through the reaction of one or more first reagents housed in the first compartment of the cartridge and one or more second reagents housed in the second compartment of the cartridge.

As described further below, advantageously the cartridge assembly of the invention may be used in an aerosol-generating system for the in situ generation of an aerosol comprising nicotine salt particles that is inhalable into a user's lungs.

In the retracted position the first and second air inlets and the first and second air outlets of the first and second compartments, respectively, of the cartridge are obstructed by the mouthpiece. As a result, in the retracted position the first and second airflow pathways through the cartridge are both obstructed and air is substantially prevented from being drawn through the first and second compartments of the cartridge along the first and second airflow pathways.

Advantageously, due to the obstruction of the first and second air inlets and the first and second air outlets of the first and second compartments, respectively, of the cartridge by the mouthpiece, in use, in the retracted position loss of the first and second reagents housed in the first and second compartments of the cartridge from the cartridge assembly may be substantially prevented. Advantageously, by storing the cartridge assembly with the cartridge and the mouthpiece in the retracted position, sufficient first and second reagents may thus be retained in the cartridge assembly to generate a desired aerosol for delivery to a user upon initial use of an aerosol-generating system comprising the cartridge assembly.

Advantageously, by moving the cartridge and the mouthpiece of the cartridge assembly relative to one another from the extended position to the retracted position between uses of an aerosol-generating system comprising the cartridge assembly, sufficient first and second reagents may also be retained in the cartridge assembly to generate a desired aerosol for delivery to a user upon one or more subsequent uses of the aerosol-generating system.

In addition, due to the obstruction of the first and second air inlets and the first and second air outlets of the first and second compartments, respectively, of the cartridge by the mouthpiece, in the retracted position the first and second compartments are not in fluid communication with one another. Advantageously, in the retracted position reaction between first and second reagents housed in the first and second compartments of the cartridge may thus be substantially prevented.

As used herein with reference to the invention, the terms "proximal", "distal", "upstream" and "downstream" are used to describe the relative positions of components, or portions of components, of the cartridge assembly or aerosol-generating system.

The cartridge assembly has a proximal end through which, in use, an aerosol exits the cartridge assembly for delivery to a user. The proximal end of the cartridge assembly may also be referred to as the mouth end. In use, in the extended position a user draws on the proximal end of the cartridge assembly in order to inhale an aerosol generated by an aerosol-generating system comprising the cartridge assembly. The cartridge assembly has a distal end opposed to the proximal end.

The mouthpiece is at the proximal end of the cartridge assembly. The cartridge assembly is at the proximal end of the aerosol-generating system. The aerosol-generating system has a distal end opposed to the proximal end.

Components or portions of components, of the cartridge assembly or aerosol-generating system may be described as being upstream or downstream of one another based on their relative positions between the proximal end and the distal end of the cartridge assembly or aerosol-generating system.

The first and second air outlets are located at the proximal end of the cartridge. The first air inlet is located upstream of the first air outlet and the second air inlet is located upstream of the second air outlet. The third air outlet is located at the proximal end of the mouthpiece.

The cartridge and the mouthpiece of the cartridge assembly are configured so that a user may manually move the cartridge and the mouthpiece relative to one another along a longitudinal axis of the cartridge assembly between the retracted position and the extended position.

As used herein with reference to the invention, the term "longitudinal" is used to describe the direction between the proximal end and the opposed distal end of the cartridge assembly or aerosol-generating system and the term "transverse" is used to describe the direction perpendicular to the longitudinal direction.

Advantageously, the cartridge and the mouthpiece are slidable relative to one another between the retracted position and the extended position.

The length of the cartridge assembly in the extended position is greater than the length of the cartridge assembly in the retracted position. In the retracted position, the proximal end of the mouthpiece abuts the proximal end of the cartridge. In the extended position, the proximal ends of the mouthpiece and the cartridge are longitudinally spaced apart so as to create a chamber therebetween.

As used herein with reference to the invention, by "length" is meant the maximum longitudinal dimension between the distal end and the proximal end of components, or portions of components, of the cartridge assembly or aerosol-generating system.

Advantageously, the first compartment has a transverse first air inlet and a longitudinal first air outlet and the second compartment has a transverse second air inlet and a longitudinal second air outlet.

As used herein with reference to the invention, the term "transverse air inlet" is used to describe one or more apertures through which air may be drawn in a transverse direction into a component or portion of a component of the cartridge assembly.

As used herein with reference to the invention, the term "longitudinal air outlet" is used to describe one or more apertures through which air may be drawn in a longitudinal direction out of a component or portion of a component of the cartridge assembly.

Advantageously, the cartridge is substantially cylindrical and the first compartment has a radial first air inlet and a longitudinal first air outlet and the second compartment has a radial second air inlet and a longitudinal second air outlet.

Advantageously, the mouthpiece has a longitudinal third air outlet.

Advantageously, the mouthpiece has a third air inlet, wherein in the retracted position the third air inlet is obstructed by the cartridge, and wherein in the extended position air may be drawn into the chamber through the third air inlet and out of the chamber through the third air outlet.

Advantageously, in use, in the extended position a third air stream may be drawn into the chamber through the third air inlet of the mouthpiece to dilute the aerosol formed by the reaction of the one or more first reagents entrained in the first air stream and the one or more second reagents entrained in the second air stream.

Advantageously, the mouthpiece has a transverse third air inlet.

Advantageously, the mouthpiece is substantially cylindrical and has a radial third air outlet.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two three or four apertures.

The first air inlet of the first compartment of the cartridge and the second air inlet of the second compartment of the cartridge may comprise the same or different numbers of apertures.

Advantageously, the first air inlet of the first compartment of the cartridge and the second air inlet of the second compartment of the cartridge each comprise a plurality of spaced apart apertures.

Advantageously, the first air inlet of the first compartment of the cartridge and the second air inlet of the second compartment of the cartridge each comprise a plurality of spaced apart transverse apertures.

Advantageously, the cartridge is substantially cylindrical and the first air inlet of the first compartment of the cartridge and the second air inlet of the second compartment of the cartridge each comprise a plurality of circumferentially spaced apart radial apertures.

The number, dimensions and location of the apertures forming the first air inlet of the first compartment of the cartridge and the number, dimensions and location of the apertures forming the second air inlet of the second compartment of the cartridge may be chosen to provide a desired airflow through the first compartment and the second compartment of the cartridge, respectively.

For example, increasing the number of apertures forming the first air inlet of the first compartment of the cartridge and the number of apertures forming the second air inlet of the second compartment of the cartridge may result in more homogeneous airflow within the first compartment and the second compartment, respectively. In use, this may advantageously improve entrainment of one or more first reagents housed in the first compartment in a first air stream drawn along the first airflow pathway through the first compartment between the first air inlet and the first air outlet and improve entrainment of one or more second reagents housed in the second compartment in a second air stream drawn along the second airflow pathway through the second compartment between the second air inlet and the second air outlet, and out of the cartridge through the second air outlet.

The apertures forming the first air inlet of the first compartment of the cartridge and the apertures forming the second air inlet of the second compartment of the cartridge may be arranged symmetrically with respect to each other.

Advantageously, the cartridge is substantially cylindrical and the apertures forming the first air inlet of the first compartment of the cartridge and the apertures forming the second air inlet of the second compartment of the cartridge are arranged symmetrically about the major axis of the cartridge.

The dimensions of the first compartment of the cartridge may be chosen to allow a desired amount of one or more first reagents to be housed in the cartridge.

The dimensions of the second compartment of the cartridge may be chosen to allow a desired amount of one or more second reagents to be housed in the cartridge.

The ratio of first and second reagents housed in the cartridge required to achieve an appropriate reaction stoichiometry in the first and second air streams may be controlled and balanced through variation of the volume of the first compartment relative to the volume of the second compartment. For example, to achieve an appropriate reaction stoichiometry the volume of the first compartment may be less than the volume of the second compartment.

The ratio of first and second reagents required to achieve an appropriate reaction stoichiometry in the first and second air streams may be controlled and balanced through variation of the volumetric airflow through the first compartment of the cartridge relative to the volumetric airflow through the second compartment of the cartridge in the extended position. The ratio of the volumetric airflow through the first compartment relative to the volumetric airflow through the second compartment may be controlled through variation of one or more of the number, dimensions and location of the apertures forming the first air inlet of the first compartment of the cartridge relative to the number, dimensions and location of the apertures forming the second air inlet of the second compartment of the cartridge.

The first compartment the second compartment of the cartridge may be arranged symmetrically with respect to each other within the cartridge.

Advantageously, the cartridge is substantially cylindrical and the first compartment and the second compartment of the cartridge are arranged symmetrically about the major axis of the cartridge.

The first air outlet of the first compartment of the cartridge and the second air outlet of the second compartment of the cartridge may each comprise one or more apertures. For example, the first air outlet of the first compartment of the cartridge and the second air outlet of the second compartment of the cartridge may each comprise one, two three or four apertures.

The first air outlet of the first compartment of the cartridge and the second air outlet of the second compartment of the cartridge may comprise the same or different numbers of apertures.

Advantageously, the first air outlet of the first compartment of the cartridge of the cartridge assembly and the second air outlet of the second compartment of the cartridge of the cartridge assembly may each comprise a single aperture.

Advantageously, the first air outlet of the first compartment of the cartridge of the cartridge assembly and the second air outlet of the second compartment of the cartridge of the cartridge assembly each comprise a single longitudinal aperture.

The number, dimensions and location of the apertures forming the first air outlet of the first compartment of the cartridge and the number, dimensions and location of the apertures forming the second air outlet of the second compartment of the cartridge may be chosen to provide a desired airflow through the first compartment and the second compartments of the cartridge, respectively.

Reducing the number of the apertures forming the first air outlet of the first compartment of the cartridge and the number of the apertures forming the second air outlet of the second compartment of the cartridge may advantageously simplify manufacturing of the cartridge assembly.

Increasing the dimensions of the apertures forming the first air outlet of the first compartment of the cartridge and the dimensions of the apertures forming the second air outlet of the second compartment of the cartridge may advantageously reduce the risk of the first air outlet of the first compartment of the cartridge and the second air outlet of the second compartment of the cartridge becoming obstructed by, for example, dust.

Preferably, the cartridge assembly comprises a resilient seal around the first air inlet that is compressed by the mouthpiece in the retracted position. Advantageously, this helps to ensure that airflow into the cartridge through the first air inlet is substantially prevented in the retracted position.

Preferably, the cartridge assembly comprises a resilient seal around the first air outlet that is compressed by the mouthpiece in the retracted position. Advantageously, this helps to ensure that airflow out of the cartridge through the first air outlet is substantially prevented in the retracted position.

Preferably, the cartridge assembly comprises a resilient seal around the second air inlet that is compressed by the mouthpiece in the retracted position. Advantageously, this helps to ensure that airflow into the cartridge through the second air inlet is substantially prevented in the retracted position.

Preferably, the cartridge assembly comprises a resilient seal around the second air outlet that is compressed by the mouthpiece in the retracted position. Advantageously, this helps to ensure that airflow out of the cartridge through the second air outlet is substantially prevented in the retracted position.

Advantageously, the cartridge assembly comprises resilient seals around each of the first air inlet, first air outlet, second air inlet and second air outlet that are compressed by the mouthpiece in the retracted position. Advantageously, this helps to ensure that the air is substantially prevented from being drawn through the first and second compartments of the cartridge along the first and second airflow pathways in the retracted positions.

The resilient seals may be formed from elastomeric materials such as, for example, rubbers and silicones. The resilient seals may be formed on the outer surface of the cartridge by, for example, overmoulding. The resilient seals may be integral with and formed of the same material as the cartridge.

The cartridge of the cartridge assembly may further comprise a first guide element and the mouthpiece of the cartridge assembly may comprise a second guide element that cooperate with one another to guide longitudinal movement of the cartridge and the mouthpiece relative to one another between the retracted position and the extended position.

Advantageously, the first guide element comprises one or more grooves on an outer surface of the cartridge and the second guide element comprises one or more projections on an inner surface of the mouthpiece.

The cartridge and the mouthpiece of the cartridge assembly may be formed from the same or different materials.

The cartridge and the mouthpiece of the cartridge assembly may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins and vinyl resins.

The cartridge may be formed from one or more materials that are nicotine-resistant and lactic acid-resistant.

Advantageously, the cartridge and mouthpiece of the cartridge assembly are formed from one or more materials selected from the group consisting of polyether ether ketone (PEEK), polyoxymethylene (POM), high-density polyethylene (HDPE) and other semicrystalline thermoplastic polymers.

The cartridge and mouthpiece of the cartridge assembly may be formed by any suitable method. Suitable methods include, but are not limited to, deep drawing, injection moulding, blistering, blow forming and extrusion.

The cartridge of the cartridge assembly may be designed to be disposed of once the first and second reagents in the first and second compartments are depleted.

The cartridge of the cartridge assembly may be designed to be refillable.

The mouthpiece of the cartridge assembly may be designed to be disposed of once the first and second reagents in the first and second compartments of the cartridge are depleted.

The mouthpiece of the cartridge assembly may be designed to be reusable.

In embodiments in which the cartridge and the mouthpiece of the cartridge assembly are both designed to be disposed of once the first and second reagents in the first and second compartments the cartridge are depleted, the entire cartridge assembly may be discarded after use.

The cartridge may have any suitable shape. Preferably, the cartridge is substantially cylindrical. As used herein with reference to the invention, the terms "cylinder" and "cylindrical" refer to a substantially right circular cylinder with a pair of opposed substantially planar end faces.

The cartridge may have any suitable size. The cartridge may have a length of, for example, between about 5 mm and about 50 mm. For example, the cartridge may have a length of about 40 mm. The cartridge may have a diameter of, for example, between about 4 mm and about 10 mm. For example, the cartridge may have a diameter of between about 7 mm and about 8 mm.

The cartridge assembly may simulate the shape and dimensions of a combustible smoking article, such as a cigarette, a cigar, or a cigarillo. Advantageously, the cartridge assembly simulates the shape and dimensions of a cigarette.

As described further below, advantageously the cartridge further comprises a cavity for receiving a heater configured to heat the first compartment and the second compartment.

Advantageously, the cartridge is substantially cylindrical and the cavity extends along the major axis of the cartridge. In such embodiments, the cavity is preferably located between the first and second compartments, that is the first and second compartments are preferably disposed on either side of the cavity.

Advantageously, the cartridge assembly is for use in an aerosol-generating system for the in situ generation of an aerosol of nicotine salt particles and the first compartment of the cartridge of the cartridge assembly comprises a nicotine source and the second compartment of the cartridge of the cartridge assembly comprises an acid source. In such embodiments, the cartridge and the mouthpiece are preferably formed from one or more materials that are nicotine-resistant and acid-resistant.

The nicotine source may comprise one or more of nicotine, nicotine base, a nicotine salt, such as nicotine-HCl, nicotine-tartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments the nicotine source may comprise an aqueous solution of nicotine, nicotine base, a nicotine salt or a nicotine derivative and an electrolyte forming compound.

The nicotine source may further comprise other components including, but not limited to, natural flavours, artificial flavours and antioxidants.

The nicotine source may comprise a sorption element and nicotine sorbed on the sorption element.

The sorption element may be formed from any suitable material or combination of materials. For example, the sorption element may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The sorption element may be a porous sorption element. For example, the sorption element may be a porous sorption element comprising one or more materials selected from the group consisting of porous plastic materials, porous polymer fibres and porous glass fibres.

The sorption element is preferably chemically inert with respect to nicotine.

The sorption element may have any suitable size and shape.

In certain embodiments the sorption element may be a substantially cylindrical plug. For example, the sorption element may be a porous substantially cylindrical plug.

In other embodiments the sorption element may be a substantially cylindrical hollow tube. For example, the sorption element may be a porous substantially cylindrical hollow tube.

The size, shape and composition of the sorption element may be chosen to allow a desired amount of nicotine to be sorbed on the sorption element.

The sorption element advantageously acts as a reservoir for the nicotine.

The acid source may comprise an organic acid or an inorganic acid. Preferably, the acid source comprises an organic acid, more preferably a carboxylic acid, most preferably lactic acid or an alpha-keto or 2-oxo acid.

Advantageously, the acid source comprises an acid selected from the group consisting of lactic acid, 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. Advantageously, the acid source comprises lactic acid or pyruvic acid.

The acid source may comprise a sorption element and acid sorbed on the sorption element.

The sorption element may be formed from any suitable material or combination of materials, for example those listed above.

The sorption element is preferably chemically inert with respect to the acid.

The sorption element may have any suitable size and shape.

In certain embodiments the sorption element may be a substantially cylindrical plug. For example, the sorption element may be a porous substantially cylindrical plug.

In other embodiments the sorption element may be a substantially cylindrical hollow tube. For example, the sorption element may be a porous substantially cylindrical hollow tube.

The size, shape and composition of the sorption element may be chosen to allow a desired amount of acid to be sorbed on the sorption element.

The sorption element advantageously acts as a reservoir for the acid.

According to the invention there is provided an aerosol-generating system comprising a cartridge assembly according to the invention and a heater for heating one or both of the first and second compartments of the cartridge of the cartridge assembly.

Advantageously, in use, in the extended position heating one or both of the first compartment and the second compartment of the cartridge of the cartridge assembly to a temperature above ambient temperature enables the vapour concentrations of the first and second reagents in the first and second compartments, respectively, of the cartridge to be controlled and balanced proportionally to yield an efficient reaction stoichiometry of the first and second reagents in the first and second air streams. Advantageously, this may improve the efficiency of the formation of an aerosol and the consistency of delivery to a user. Advantageously, it may also reduce the delivery of unreacted first reagent vapour and unreacted second reagent vapour to a user.

Advantageously, the first compartment of the cartridge of the cartridge assembly comprises a nicotine source and the second compartment of the cartridge of the cartridge assembly comprises an acid source. In such embodiments, the heater is preferably configured to heat both the nicotine source and the acid source. In certain preferred embodiments, the heater is configured to heat both the nicotine source and the acid source to a temperature of below about 250 degrees Celsius (° C.). Advantageously, the heater is configured to heat both the nicotine source and the acid source to a temperature of between about 80° C. and about 150° C.

Advantageously, the heater may be configured to heat the nicotine source and the acid source to substantially the same temperature.

As used herein with reference to the invention, by "substantially the same temperature" it is meant that the difference in temperature of the nicotine source and the acid source measured at corresponding locations relative to the heater is less than about 3° C.

The heater may have any shape suitable to heat one or both of the first compartment and the second compartment.

The heater may be an external heater. As used herein with reference to the invention, the term "external heater" refers to a heater that in use is positioned externally to the cartridge of the cartridge assembly.

The heater may be an internal heater. As used herein with reference to the invention, the term "internal heater" refers to a heater that in use is positioned internally to the cartridge of the cartridge assembly.

Preferably, the aerosol-generating system comprises a single heater for heating both of the first and second compartments of the cartridge of the cartridge assembly. More preferably, the aerosol-generating system comprises a single internal heater for heating both of the first and second compartments of the cartridge of the cartridge assembly.

The aerosol-generating system may further comprise a power supply for supplying power to the heater and a controller configured to control a supply of power from the power supply to the heater.

The aerosol-generating system may comprise a controller configured to control a supply of power from an external power supply to the heater.

The aerosol-generating system may further comprise one or more temperature sensors configured to sense the temperature of the heater and the first and second compartments of the cartridge of the cartridge assembly. In such embodiments, the controller may be configured to control a supply of power to the heater based on the sensed temperature.

Preferably, the heater comprises an electric heating element powered by an electric power supply. Where the heater comprises an electric heating element, the aerosol-generating system may further comprise an electric power supply and a controller comprising electronic circuitry configured to control the supply of electric power from the electric power supply to the electric heating element. Any suitable electronic circuitry may be used in order to control the supply of power to the electric heating element. The electronic circuitry may be programmable.

The power supply may be a DC voltage source. In certain preferred embodiments of the invention, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may be another form of charge storage device such as a capacitor. The power supply may require recharging. The power supply may have a capacity that allows for the storage of enough energy for use of the heater with one or more cartridge assemblies.

Preferably, the electric heating element comprises an electrically resistive material. The electric heating element may comprise a non-elastic material, for example a ceramic sintered material, such as alumina ($Al_2O_3$) and silicon nitride ($Si_3N_4$), or printed circuit board or silicon rubber. The electric heating element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The electric heating element may be formed using a metal having a defined relationship between temperature and resistivity. In such embodiments, the metal may be formed as a track between two layers of suitable insulating materials. An electric heating element formed in this manner may be used both as a heater and a temperature sensor.

The heater may be powered by a non-electric power supply, such as a combustible fuel. For example, the heater may comprise a thermally conductive element that is heated by combustion of a gaseous fuel.

The heater may be a non-electric heating means, such as a chemical heating means.

In certain embodiments the heater may comprise a heat sink or heat exchanger configured to transfer thermal energy from an external heat source to one or both of the first and second compartments of the cartridge assembly. The heat sink or heat exchanger may be formed of any suitable thermally conductive material. Suitable thermally conductive materials include, but are not limited to, metals, such as aluminium and copper.

According to a preferred embodiment of the invention there is provided an aerosol-generating system comprising the cartridge assembly and an aerosol-generating device comprising a heater for heating one or both of the first and second compartments of the cartridge of the cartridge assembly.

As used herein with reference to the invention, the term "aerosol-generating device" refers to a device that is configured to interact with a cartridge assembly according to the invention to generate an aerosol.

According to a particularly preferred embodiment of the invention there is provided an aerosol-generating system comprising a cartridge assembly according to the invention and an aerosol-generating device comprising a cavity for at least partially receiving the cartridge assembly and a heater for heating one or both of the first and second compartments of the cartridge of the cartridge assembly.

Advantageously, the aerosol-generating system comprises a consumable cartridge assembly according to the invention and a reusable aerosol-generating device comprising a heater for heating one or both of the first and second compartments of the cartridge of the cartridge assembly.

Advantageously, the aerosol-generating system comprises a consumable cartridge assembly according to the invention and a reusable aerosol-generating device comprising a cavity for at least partially receiving the cartridge assembly and a heater for heating one or both of the first and second compartments of the cartridge of the cartridge assembly.

Where the aerosol-generating device comprises a cavity for at least partially receiving the cartridge assembly, the cavity of the aerosol-generating device is preferably substantially cylindrical.

Preferably, the cavity of the aerosol-generating device has a diameter substantially equal to or slightly greater than the diameter of the cartridge assembly.

Preferably, the length of the cavity of the aerosol-generating device is less than the length of the cartridge assembly so that when the cartridge assembly is inserted into the cavity of the aerosol-generating device at least the proximal end of the mouthpiece of the aerosol-cartridge assembly projects from the cavity of the aerosol-generating device in the extended position.

The aerosol-generating device may comprise an external heater positioned about a perimeter of the cavity.

Advantageously, the cartridge of the cartridge assembly further comprises a cavity and the aerosol-generating device comprises an internal heater configured to be received in the cavity of the cartridge of the cartridge assembly.

In such embodiments, the aerosol-generating device may further comprise a guide element configured for engagement with the cartridge assembly to facilitate proper alignment of the internal heater of the aerosol-generating device with the cavity in the cartridge of the cartridge assembly.

Advantageously, the internal heater of the aerosol-generating device is an elongate internal electric heating element having a width that is greater than the thickness thereof so that the elongate internal electric heating element is in the form of a heater blade, which is configured to be received in the cavity of the cartridge of the cartridge assembly. In such embodiments, the cavity in the cartridge of the cartridge assembly may be configured as an elongate slot.

For the avoidance of doubt, features described above in relation to one aspect of the invention may also be applicable to other aspects of the invention. In particular, features described above in relation to the cartridge assembly of the invention may also relate, where appropriate, to the aerosol-generating system of the invention, and vice versa.

Embodiments of the invention will now be described, by way of example only, with reference to the accompanying drawings, in which:

FIG. 1 shows a schematic longitudinal cross-section of an example of a cartridge for use in a cartridge assembly according to the invention;

FIG. 2 shows a plan view of the distal end of the cartridge shown in FIG. 1;

FIG. 3 shows a plan view of the proximal end of the cartridge shown in FIG. 1;

FIGS. 1 to 4 are schematic illustrations of an example of a cartridge for use in a cartridge assembly according to the invention for use in an aerosol-generating system for generating an aerosol comprising nicotine salt particles. In this example, the cartridge 2 is cylindrical with a substantially circular transverse cross-section and comprises a first compartment 4 comprising a nicotine source and a second compartment 6 comprising an acid source. The nicotine source may comprise a sorption element, such as a PTFE wick, with nicotine adsorbed thereon, which is inserted into the first compartment 4. The acid source may comprise a sorption element, such as a PTFE wick, with acid adsorbed thereon, which is inserted into the second compartment 6. The acid may be, for example, lactic acid.

The cartridge 2 further comprises a cavity 8 that extends along the major axis of the cartridge 2 from the distal end of the cartridge 2 part way along the length of the cartridge 2. The cavity may, be configured as a slot and may, for example, have a length of about 15 mm, a width of about 6 mm and a height of about 0.8 mm.

The first compartment 4 and the second compartment 6 are of substantially semi-circular transverse cross-section and are disposed on either side of the cavity 8 and extend from the proximal end of the cartridge 2 part way along the length of the cartridge 2. The first and second compartments may, for example, have a radius of about 3.5 mm and the distance between the first and second compartments and the cavity may, for example, be about 0.5 mm.

The first compartment has a first air inlet and a first air outlet and the second compartment has a second air inlet and a second air outlet. The first air inlet and the first air outlet are separate, distinct apertures in the first compartment and the second air inlet and the second air outlet are separate, distinct apertures in the second compartment.

Figure 4:
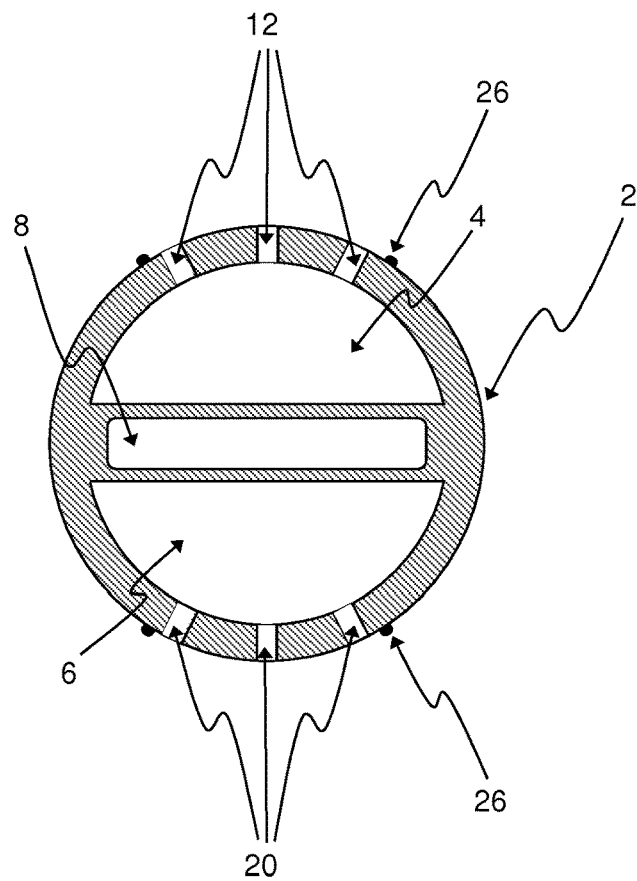
FIG. 4 shows a schematic transverse cross-section view of the cartridge shown in FIG. 1 along the line A-A.

As shown in FIGS. 1, 3 and 4, the first compartment 4 has a first air inlet 10 comprising three circumferentially spaced apart, radial apertures 12 near the distal end thereof and a first air outlet 14 comprising a single longitudinal aperture 16 at the proximal end thereof. The first air outlet 14 is in fluid communication with the first air inlet 10 so that air may pass into the cartridge 2, through the radial apertures 12, through the first compartment 4 and out of the cartridge 2 though the longitudinal aperture 20.

Similarly, the second compartment 6 has a second air inlet 18 comprising three circumferentially spaced apart, radial apertures 20 near the distal end of and thereof and a second air outlet 22 comprising a single longitudinal aperture 24 at the proximal end thereof. The second air outlet 16 is in fluid communication with the second air inlet 18 so that air may pass into the cartridge 2 through the radial apertures 20, through the second compartment 6 and out of the cartridge 2 though the longitudinal aperture 24.

The first compartment and the second compartment are arranged in parallel within the cartridge.

As used herein with reference to the invention, by "parallel" it is meant that the first compartment and the second compartment are arranged within the cartridge so that in the extended position a first air stream may be drawn through the first compartment along a first airflow pathway between the first air inlet and the first air outlet of the first compartment of the cartridge and a second air stream may be drawn through the second compartment along a second airflow pathway between the second air inlet and the second air outlet of the second compartment of the cartridge.

As shown in FIGS. 2 and 4, the radial apertures 12 and 20 of the first 10 and second 18 air inlets, respectively, are each surrounded by a resilient seal 26 that projects outwardly from the circumferential surface of the cartridge 2.

As shown in FIG. 3, the longitudinal apertures 16 and 24 of the first 14 and second 22 air outlets, respectively, are each surrounded by a resilient seal 28 that projects outwardly from the surface of the proximal end of the cartridge 2.

The resilient seals 26 and 28 surrounding the radial apertures 12 and 20 of the first 10 and second 18 air inlets and the longitudinal apertures 16 and 24 of the first 14 and second 22 air outlets, respectively, may be formed from elastomeric materials such as, for example, rubbers and silicones. In such embodiments, the resilient seals 26 and 28 may be formed on the outer surface of the cartridge 2 by, for example, overmoulding. Alternatively, the resilient seals 26 and 28 may be integral with and formed of the same material as the cartridge 2. In such embodiments, the cartridge 2 and the resilient seals 26 and 28 may be formed from semicrystalline thermoplastic polymers such as, for example, polyether ether ketone (PEEK), polyoxymethylene (POM) and high-density polyethylene (HDPE).

The cartridge 2 may have a diameter of about 8 mm and the resilient seals 26 and 28 may have a height of for example, between about 0.05 mm and about 0.25 mm.

Figure 5:
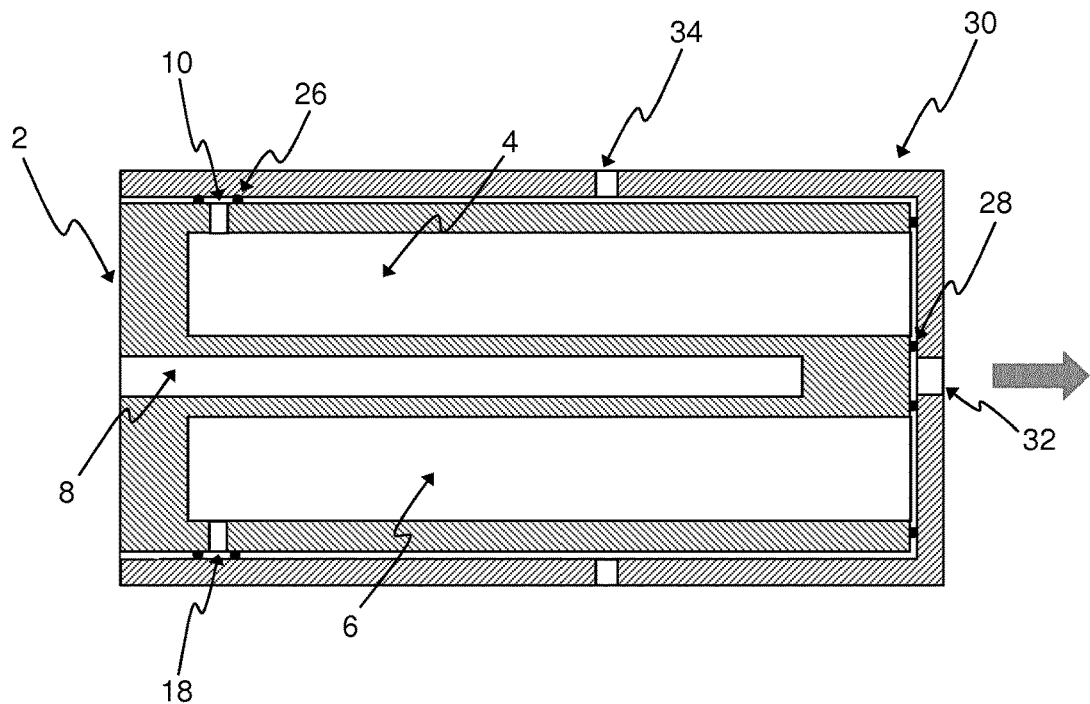
FIG. 5 shows a schematic longitudinal cross-section of a cartridge assembly according to an embodiment of the invention comprising the cartridge shown in FIGS. 1 to 4 and a mouthpiece with the mouthpiece in a retracted position.
Figure 6:
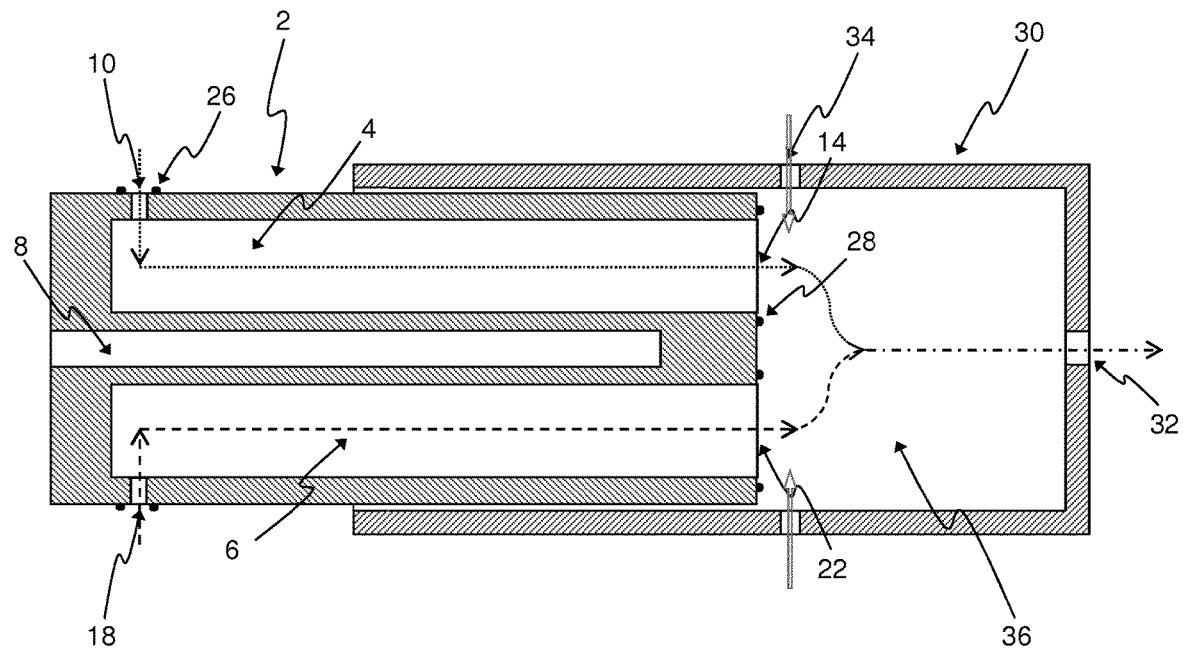
FIG. 6 shows a schematic longitudinal cross-section of the cartridge assembly shown in FIG. 2 with the mouthpiece in an extended position.

FIGS. 5 and 6 are schematic illustrations of a cartridge assembly according to an embodiment of the invention comprising the cartridge shown in FIGS. 1 to 4 and a mouthpiece 30.

The mouthpiece 30 comprises a cylindrical cavity of circular cross-section that extends along the major axis of the mouthpiece 30 from the distal end of the mouthpiece 30 part way along the length of the mouthpiece 30 and that is configured to receive the cartridge 2. To form the cartridge assembly, the proximal end of the cartridge 2 is inserted into the distal end of the cavity of the mouthpiece 30 such that the inner circumferential surface of the cavity of the mouthpiece 30 at least partially overlies the outer circumferential surface of the cartridge 2.

The mouthpiece has a third air outlet 32 comprising a single central longitudinal aperture at the proximal end thereof and has a third air inlet 34 comprising a plurality of circumferentially spaced apart, radial apertures 36 between the proximal end and the distal end thereof. The third air outlet 34 is in fluid communication with the third air inlet 34 so that air may pass into the mouthpiece, through the radial apertures, through the cavity and out of the mouthpiece 30 though the longitudinal aperture.

The cartridge 2 and the mouthpiece 30 are slidable relative to one another along the longitudinal axis of the cartridge assembly between a retracted position (shown in FIG. 5) and an extended position (shown in FIG. 6), with the block arrow in FIG. 5 indicating the direction of longitudinal movement.

The cartridge 2 may further comprise a first guide element (not shown) comprising one or more grooves on an outer surface of the cartridge 2 and the mouthpiece 30 may comprise a second guide element (not shown) comprising one or more projections on an inner surface of the mouthpiece that cooperate with one another to guide longitudinal movement of the cartridge and the mouthpiece relative to one another between the retracted position shown in FIG. 5 and the extended position shown in FIG. 6.

In the retracted position, the proximal end of the mouthpiece 30 abuts the proximal end of the cartridge 2. As shown in FIG. 5, in the retracted position the first 10 and second 18 air inlets of the first 2 and second 6 compartments, respectively, of the cartridge 2 are obstructed by the mouthpiece 30. This prevents air from being drawn into the cartridge 2 through the first 10 and second 18 air inlets. In the retracted position, the resilient seals 26 surrounding the radial apertures 12 and 20 of the first 10 and second 18 air inlets of the first 2 and second 6 compartments, respectively, of the cartridge 2 are compressed between the outer circumferential surface of the cartridge 2 and the inner circumferential surface of the cavity of the mouthpiece 30. This helps to ensure that airflow into the cartridge 2 through the first 10 and second 18 air inlets is substantially prevented despite manufacturing tolerances.

In the retracted position the first 14 and second 12 air outlets of the first 2 and second 6 compartments, respectively, of the cartridge 2 are also obstructed by the mouthpiece 30. This prevents air from being drawn out of the cartridge 2 through the first 14 and second 12 air outlets. In the retracted position, the resilient seals 28 surrounding the longitudinal apertures 12 and 20 of the first 14 and second 12 air outlets of the first 2 and second 6 compartments, respectively, of the cartridge 2 are compressed between the outer surface of the proximal end of the cartridge 2 and the inner surface of the proximal end of the mouthpiece 30. This helps to ensure that airflow out of the cartridge 2 through the first 14 and second 12 air outlets is substantially prevented despite manufacturing tolerances.

Obstruction of the first 10 and second 18 air inlets and the first 14 and second 12 air outlets of the first 2 and second 6 compartments, respectively, of the cartridge 2 by the mouthpiece advantageously prevents loss of the nicotine from the nicotine source in the first compartment 4 of the cartridge 2 and loss of acid from the acid source in the second compartment of the cartridge 2 in the retracted position.

As shown in FIG. 5, in the retracted position the third air inlet 36 of the mouthpiece 30 is obstructed by the cartridge. This prevents air from being drawn into the cavity of the mouthpiece 30 through the third air inlet 36. In the retracted position the third air outlet 34 of the mouthpiece 30 is also obstructed by the cartridge. This prevents air from being drawn out of the mouthpiece 30 through the third air outlet 34.

As shown in FIG. 6, in the extended position the proximal end of the mouthpiece 30 is spaced apart from the proximal end of the cartridge 2. This creates a chamber 36 between the proximal end of the cartridge 2 and the proximal end of the mouthpiece 30 defined by the outer surface of the proximal end of the cartridge 2, a proximal portion of the inner circumferential surface of the cavity of the mouthpiece 30 and the inner surface of the proximal end of the cavity of the mouthpiece 30. The chamber 36 is in fluid communication with the first 14 and second 22 air outlets of the first 2 and second 6 compartments, respectively, of the cartridge 2 and the third air inlet 34 and third air outlet of the mouthpiece 30.

In use, in the extended position a user draws on the proximal end of the mouthpiece 30 to draw air through the cartridge assembly.

As shown in FIG. 6, in the extended position the first 10 and second 18 air inlets and first 14 and second 22 air outlets of the first 2 and second 6 compartments, respectively, of the cartridge 2 and the third air outlet 32 of the mouthpiece 30 are unobstructed. This allows a first air stream (shown by dotted arrows in FIG. 6) to be drawn into the cartridge 2 through the radial apertures 12 of the first air inlet 10, along a first airflow pathway through the first compartment 4 between the first air inlet 10 and the first air outlet 14, and out of the cartridge 2 into the chamber 36 through the longitudinal aperture 16 of the first air outlet 14. It also allows a second air stream (shown by dashed arrows in FIG. 6) to be drawn into the cartridge 2 through the radial apertures 20 of the second air inlet 18, along a second airflow pathway through the second compartment 6 between the second air inlet 18 and the second air outlet 22, and out of the cartridge 2 into the chamber 36 through the longitudinal aperture 24 of the second air outlet 22.

As the first air stream is drawn along the first airflow pathway between the first air inlet 10 and the first air outlet 14 of the first compartment 4 of the cartridge 2, nicotine vapour is released from the nicotine source in the first compartment 4 into the first air stream. As the second air stream is drawn along the second airflow pathway between the second air inlet 18 and the second air outlet 22 of the second compartment 6 of the cartridge 2, acid vapour is released from the acid source in the second compartment 6 into the second air stream.

The nicotine vapour in the first air stream and the acid vapour in the second air stream react with one another in the gas phase in the chamber 36 to form an aerosol of nicotine salt particles (shown by a dashed and dotted arrow in FIG. 6), which is delivered to the user through the third air outlet 32 at the proximal end of the mouthpiece 30.

As shown in FIG. 6, in the extended position the third air inlet 34 of the mouthpiece 30 is also unobstructed. In use, when a user draws on the proximal end of the mouthpiece 30 in the extended position, this allows a third air stream (shown by block arrows in FIG. 6) to be drawn into the chamber 36 through the radial apertures of the third air inlet 34 of the mouthpiece 30 to dilute the aerosol of nicotine salt particles formed by the reaction in the gas phase of the nicotine vapour in the first air stream and the acid vapour in the second air stream.

Figure 7:
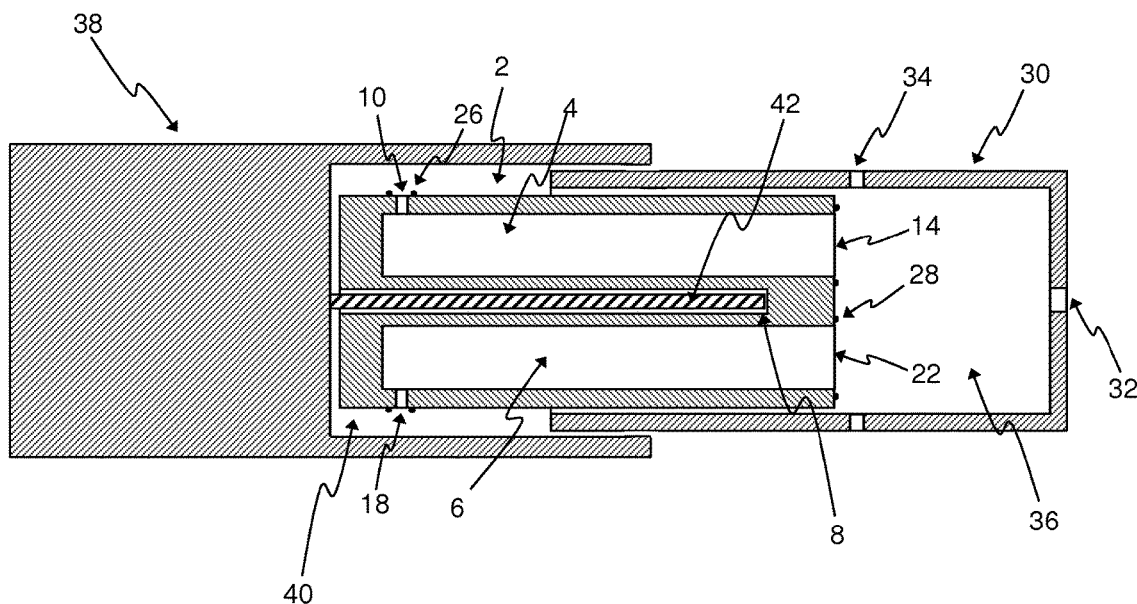
FIG. 7 shows a schematic longitudinal cross-section of an aerosol-generating system according to an embodiment of the invention comprising the cartridge assembly shown in FIG. 6 and an aerosol-generating device.

FIG. 7 is a schematic illustration of an aerosol-generating system according to an embodiment of the invention comprising the cartridge assembly shown in FIGS. 5 and 6 and an aerosol-generating device 38. In FIG. 7, the cartridge assembly is shown with the cartridge 2 and the mouthpiece 30 in the extended position.

As described further below, the cartridge assembly 2 and the aerosol-generating device 38 are configured to engage and cooperate with one another to form the aerosol-generating system.

The aerosol-generating device 38 comprises an elongate cylindrical cavity 40 of circular cross-section that extends along the major axis of the aerosol-generating device 38 from the proximal end of the aerosol-generating device 38 part way along the length of the aerosol-generating device 38 and that is configured to receive the cartridge assembly.

In use, the distal end of the cartridge assembly is inserted into the proximal end of the cavity 40 of the aerosol-generating device 38. As shown in FIG. 7, the length of the cavity 40 of the aerosol-generating device 38 is less than the length of the cartridge assembly so that when the cartridge assembly is inserted into the cavity 40 of the aerosol-generating device 38 at least the proximal end of the mouthpiece 30 of the cartridge assembly projects outwardly from the cavity 40 of the aerosol-generating device 38.

The aerosol-generating device 38 comprises a single heater 42 configured to heat both the first compartment 4 and the second compartment 6 of the cartridge 2 of the cartridge assembly. As shown in FIG. 7, the single heater 42 is positioned centrally within the cavity 40 of the aerosol-generating device 38 and extends along the major axis of the cavity 40. The single heater is an elongate electric heating element in the form of a heater blade. In the embodiment shown in FIG. 7, the length of the single heater 42 is greater than the length of the cavity 40 of the aerosol-generating device 38 and so the single heater 42 projects outwardly from the cavity 40 of the aerosol-generating device 38. However, in alternative embodiments (not shown), the length of the single heater 42 may be less than the length of the cavity 40 so that the single heater 42 does not project outwardly from the cavity 40 of the aerosol-generating device 38. The aerosol-generating device 38 further comprises a power supply (not shown) in the form of a battery and a controller (not shown) comprising electronic circuitry, which is connected to the power supply and the single heater 42.

As shown in FIG. 7, the single heater 42 of the aerosol-generating device 38 is received in the cavity 8 of the cartridge 2 of the cartridge assembly when the cartridge assembly is inserted into the cavity 40 of the aerosol-generating device 38. The elongate electrical heating element of the single heater 42 of the aerosol-generating device 106 is thus configured as an internal heater that in use is positioned internally to the cartridge assembly.

In use, once the cartridge assembly is inserted into the aerosol-generating device 38, the elongate electric heating element of the single heater 42 of the aerosol-generating device 38 heats the first compartment 4 and the second compartment 6 of the cartridge 2 of the cartridge assembly to substantially the same temperature. This increases the amount of nicotine vapour released from the nicotine source in the first compartment 4 into the first air stream drawn through the cartridge 2 of the cartridge assembly and the amount of acid vapour released into the second airstream drawn through the cartridge 2 of the cartridge assembly.

The invention has been exemplified above by reference to a cartridge assembly for use in an aerosol-generating system for the in situ generation of an aerosol of nicotine salt particles and an aerosol-generating system for the in situ generation of an aerosol of nicotine salt particles. However, it will be appreciated that the cartridge assembly and aerosol-generating system of the invention may also be advantageously used for the in situ generation of other aerosols formed by the reaction between one or more first reagents and one or more second reagents.

The invention claimed is:

1. A cartridge assembly having a proximal end and a distal end for an aerosol-generating system, the cartridge assembly comprising:
   a cartridge comprising:
      a first compartment having a first air inlet and a first air outlet,
      a second compartment having a second air inlet and a second air outlet, and
      a mouthpiece partially surrounding the cartridge, the mouthpiece having a third air outlet,
   the cartridge and the mouthpiece being longitudinally movable relative to one another between a retracted position in which a proximal end of the mouthpiece abuts a proximal end of the cartridge, and an extended position in which the proximal end of the mouthpiece and the proximal end of the cartridge are longitudinally spaced apart so as to create a chamber therebetween in fluid communication with the first, second, and third air outlets,
   wherein in the retracted position the first and second air inlets and the first and second air outlets are obstructed by the mouthpiece, and the third air outlet is obstructed by the cartridge, and
   wherein in the extended position air is drawable into the chamber along a first airflow pathway extending from the first air inlet through the first compartment to the first air outlet, and a second airflow pathway extending from the second air inlet through the second compartment to the second air outlet, and out of the chamber through the third air outlet.

2. The cartridge assembly according to claim 1, wherein the first compartment includes a transverse first air inlet and a longitudinal first air outlet, and the second compartment includes a transverse second air inlet.

3. The cartridge assembly according to claim 1, wherein the mouthpiece includes a longitudinal third air outlet.

4. The cartridge assembly according to claim 1,
wherein the mouthpiece includes a third air inlet,
wherein in the retracted position the third air inlet is obstructed by the cartridge, and
wherein in the extended position air is drawable into the chamber through the third air inlet and out of the chamber through the third air outlet.

5. The cartridge assembly according to claim 4, wherein the mouthpiece includes a transverse third air inlet.

6. The cartridge assembly according to claim 1, further comprising a resilient seal around the first air inlet that is compressed by the mouthpiece in the retracted position.

7. The cartridge assembly according to claim 1, further comprising a resilient seal around the second air inlet that is compressed by the mouthpiece in the retracted position.

8. The cartridge assembly according to claim 1, further comprising a resilient seal around the first air outlet that is compressed by the mouthpiece in the retracted position.

9. The cartridge assembly according to claim 1, further comprising a resilient seal around the second air outlet that is compressed by the mouthpiece in the retracted position.

10. The cartridge assembly according to claim 1, wherein the cartridge further comprises a first guide element and the mouthpiece further comprises a second guide element retention that cooperate to guide longitudinal movement of the cartridge and the mouthpiece relative to one another between the retracted position and the extended position.

11. The cartridge assembly according to claim 10, wherein the first guide element comprises one or more grooves on an outer surface of the cartridge and the second guide element comprises one or more projections on an inner surface of the mouthpiece.

12. The cartridge assembly according to claim 1, wherein the first compartment comprises a nicotine source and the second compartment comprises an acid source.

13. The cartridge assembly according to claim 1, wherein the cartridge further comprises a cavity configured to receive a heater configured to heat the first compartment and the second compartment.

14. An aerosol-generating system, comprising:
a cartridge assembly having a proximal end and a distal end, the cartridge assembly comprising a cartridge comprising:
  a first compartment having a first air inlet and a first air outlet,
  a second compartment having a second air inlet and a second air outlet, and
  a mouthpiece partially surrounding the cartridge, the mouthpiece having a third air outlet,
the cartridge and the mouthpiece being longitudinally movable relative to one another between a retracted position in which a proximal end of the mouthpiece abuts a proximal end of the cartridge, and an extended position in which the proximal end of the mouthpiece and the proximal end of the cartridge are longitudinally spaced apart so as to create a chamber therebetween in fluid communication with the first, second, and third air outlets,
wherein in the retracted position the first and second air inlets and the first and second air outlets are obstructed by the mouthpiece, and the third air outlet is obstructed by the cartridge, and
wherein in the extended position air is drawable into the chamber along a first airflow pathway extending from the first air inlet through the first compartment to the first air outlet, and a second airflow pathway extending from the second air inlet through the second compartment to the second air outlet, and out of the chamber through the third air outlet; and
an aerosol-generating device comprising a cavity configured to at least partially receive the cartridge assembly and a heater configured to heat one or both of the first compartment and the second compartment of the cartridge.

15. The aerosol-generating system according to claim 14, wherein the heater is disposed within the cavity of the aerosol-generating device and the cartridge comprises another cavity configured to receive the heater.

* * * * *